(12) United States Patent
Lin

(10) Patent No.: US 8,012,387 B2
(45) Date of Patent: *Sep. 6, 2011

(54) SILICONE VESICLES

(75) Inventor: Shaow Burn Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/339,154

(22) Filed: Dec. 19, 2008

(65) Prior Publication Data

US 2009/0171012 A1   Jul. 2, 2009

Related U.S. Application Data

(63) Continuation-in-part of application No. 10/592,399, filed as application No. PCT/US2005/013289 on Apr. 19, 2005, now abandoned.

(60) Provisional application No. 60/563,663, filed on Apr. 20, 2004.

(51) Int. Cl.
*B01J 13/02* (2006.01)
*C08G 77/00* (2006.01)
(52) U.S. Cl. .......................................... 264/4.1; 528/10
(58) Field of Classification Search .............. 423/447.1
See application file for complete search history.

(56) References Cited

U.S. PATENT DOCUMENTS

| | | |
|---|---|---|
| 2,823,218 A | 2/1958 | Speier et al. |
| 4,886,068 A | 12/1989 | Kaneko et al. |
| 5,364,633 A | 11/1994 | Hill et al. |
| 5,411,744 A | 5/1995 | Hill et al. |
| 5,919,487 A | 7/1999 | Simonnet et al. |
| 5,948,855 A | 9/1999 | Lin et al. |
| 5,958,433 A | 9/1999 | Simonnet |
| 5,958,448 A | 9/1999 | Ekeland et al. |
| 6,120,778 A | 9/2000 | Simonnet |
| 6,168,782 B1 | 1/2001 | Lin et al. |
| 6,632,420 B1 | 10/2003 | Cen et al. |
| 6,831,128 B2 | 12/2004 | Altes et al. |
| 6,902,722 B2 | 6/2005 | Candau et al. |
| 6,916,774 B2 | 7/2005 | Trinh et al. |
| 7,041,630 B1 | 5/2006 | Trinh et al. |
| 2003/0040571 A1 | 2/2003 | Feng et al. |
| 2003/0220425 A1 | 11/2003 | Ferritto et al. |
| 2004/0076652 A1 | 4/2004 | Paspaleeva-Kuhn et al. |
| 2004/0228821 A1 | 11/2004 | Sunkel et al. |

FOREIGN PATENT DOCUMENTS

| | | |
|---|---|---|
| EP | 0483465 | 5/1992 |
| EP | 0724876 | 8/1996 |
| WO | WO2003/038455 | 5/2003 |
| WO | WO2004/050045 | 6/2004 |

*Primary Examiner* — Robert Loewe
(74) *Attorney, Agent, or Firm* — Alan Zombeck

(57) ABSTRACT

A process for preparing a vesicle composition based upon mixing an organopolysiloxane having at least one hydrophilic substituent group, a water miscible solvent, and water is disclosed. The vesicle compositions produced by the method are useful in various personal, household, and health care applications.

10 Claims, 5 Drawing Sheets

SILICONE VESICLES

CROSS REFERENCE TO RELATED APPLICATIONS

Figure 1:
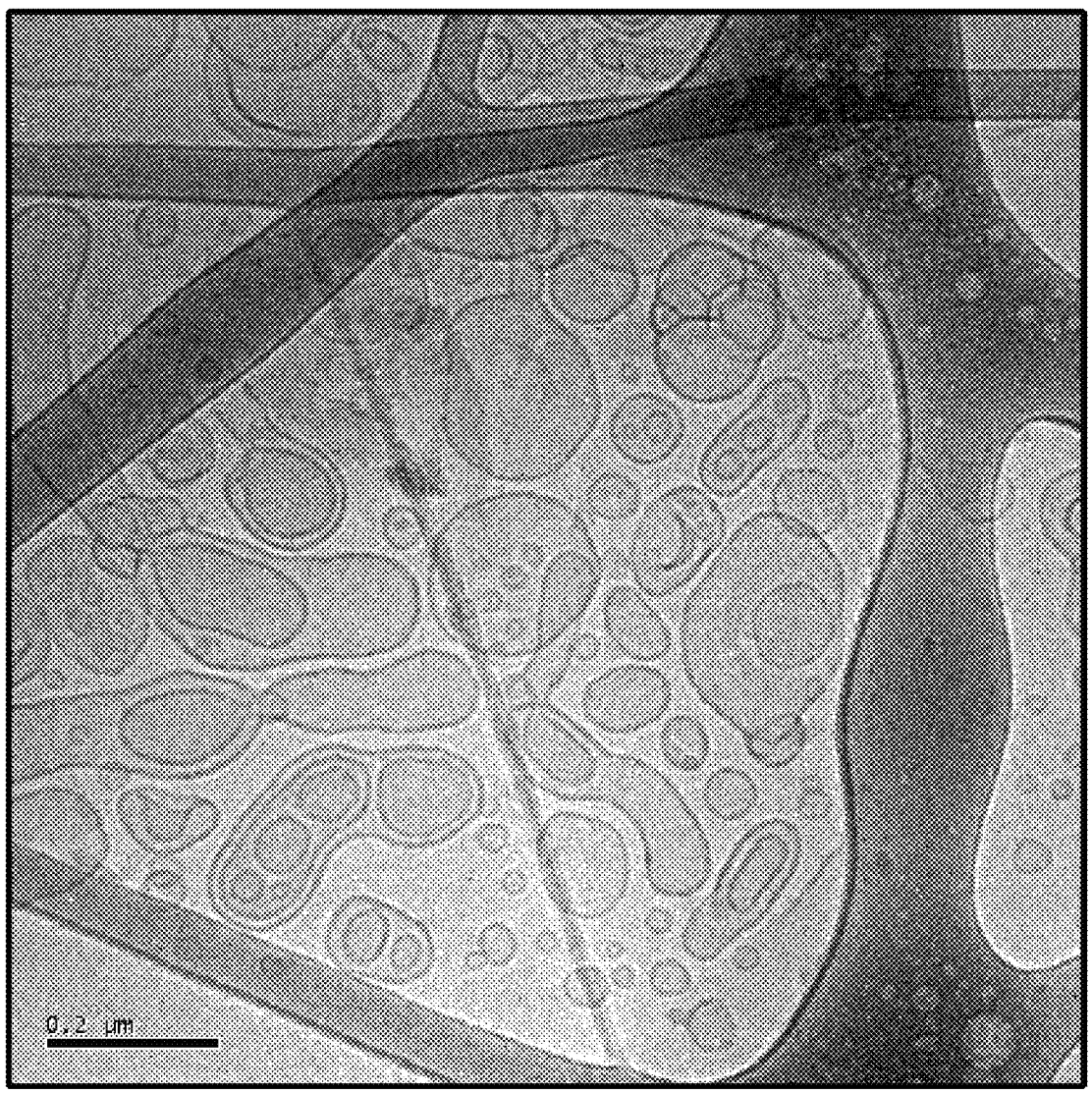
Figure 2:
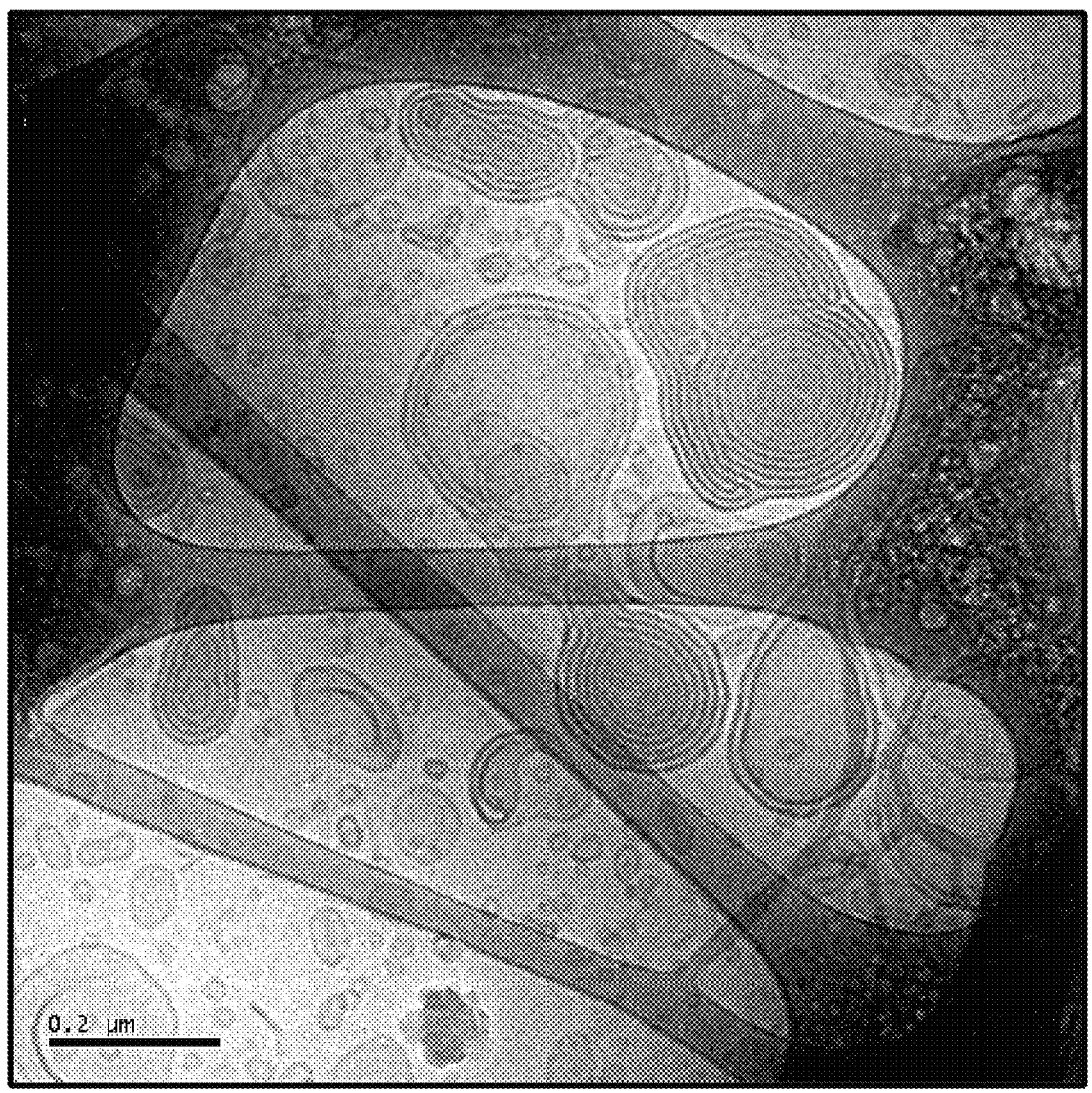
Figure 3:
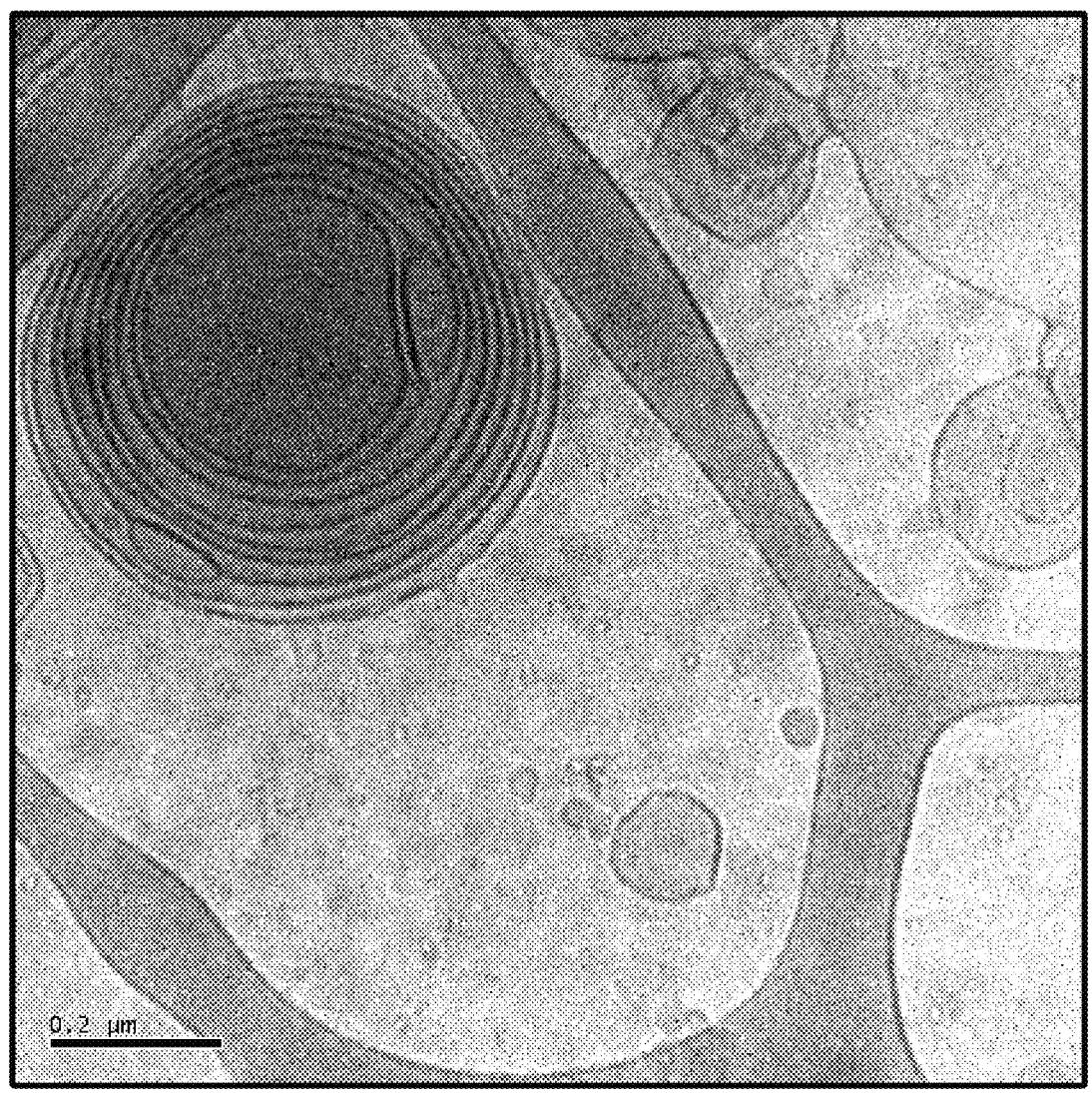
Figure 4:
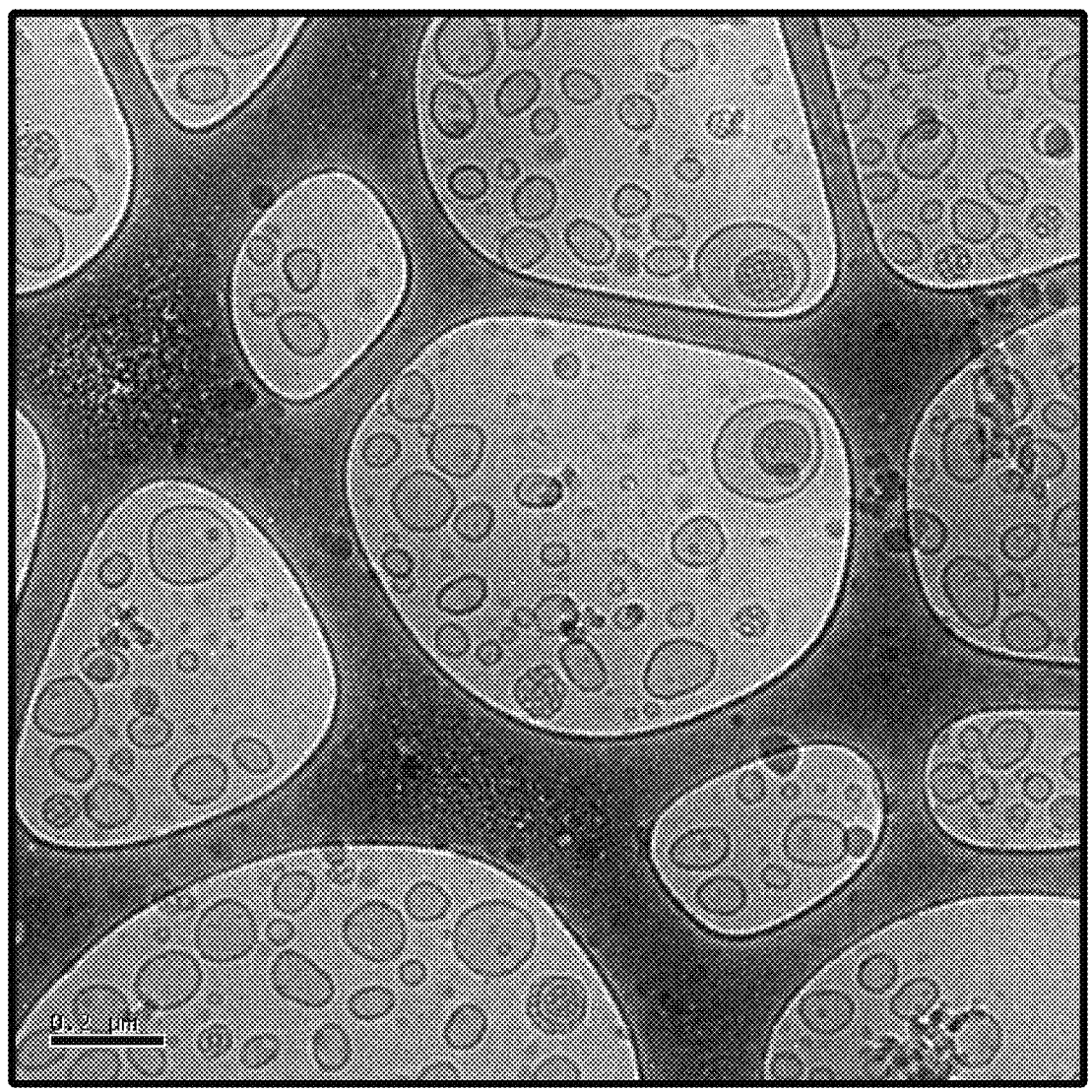
Figure 5:
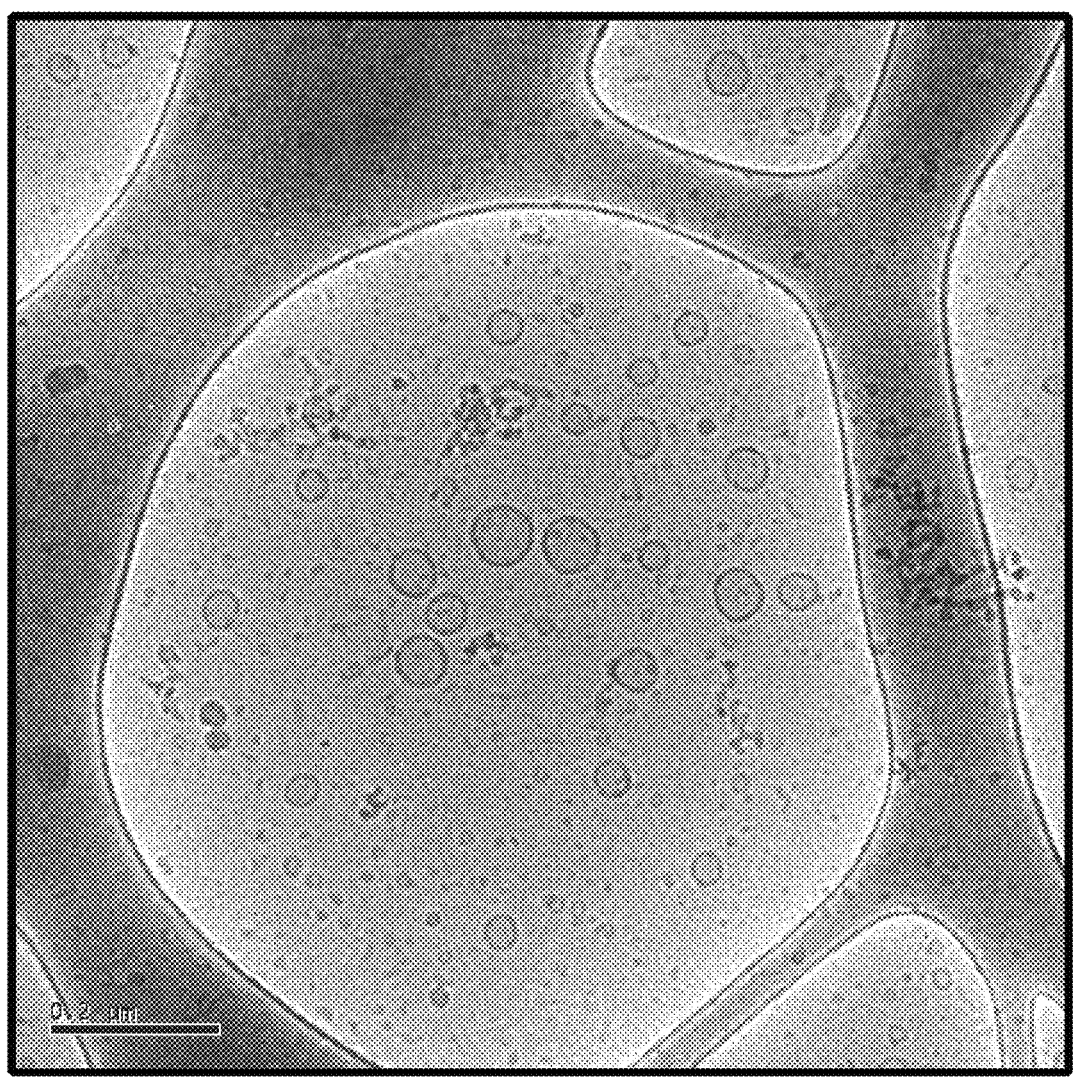

This application is a Continuation in Part of U.S. Ser. No. 10/592,399 filed on Sep. 12, 2006, now abandoned, which is a U.S. national stage filing under 35 U.S.C. §371 of PCT Application No. PCT/US05/13289 filed on 19 Apr. 2005, which claims the benefit of U.S. Provisional Patent Application No. 60/563,663 filed 20 Apr. 2004 under 35 U.S.C. §119 (e). U.S. application Ser. No. 10/592,399, PCT Application No. PCT/US05/13289 and U.S. Provisional Patent Application No. 60/563,663 are hereby incorporated by reference.

FIELD OF THE INVENTION

The present invention provides a process for preparing silicone vesicles by combining and mixing an organopolysiloxane having at least one hydrophilic substituent group, a water miscible volatile solvent, and water. The invention also relates to the vesicle compositions produced by the method and their use in various personal, household, and health care applications.

BACKGROUND OF THE INVENTION

Silicone surfactants have been designed for various applications by combining a hydrophobic organopolysiloxane with various hydrophilic moieties. For example, the silicone surfactants known as silicone polyethers are based on copolymer structures of polydimethylsiloxane having pendant polyoxyalkylene groups. Such materials find wide utility in many personal, household, and health care compositions as emulsifiers, wetting agents, and general-purpose aqueous surfactants.

The aggregation behavior of silicone polyethers has been discussed along with their ability to form vesicles. For example, U.S. Pat. Nos. 5,364,633 and 5,411,744 by Hill teaches the self-assembly of silicone vesicles in aqueous dispersions of certain silicone polyethers. PCT application US03/38455 by Lin teaches the entrapment of various oils in silicone vesicles and their use in various personal care formulations.

While these references represent advancements in the art, a need still exists to create silicone vesicles having improved stability. For example, the silicone vesicles formed from the self-assembly procedures can lack durability. This lack of durability can limit the processing conditions they can be subject to in the formation of various finished products. Furthermore, such self-assembled silicone vesicles can lack the ability to provide sustained protection of loaded actives over an extended period of time. Thus, a need exists for a process to prepare silicone vesicles having improved stability and the ability to protect loaded actives over an extended period of time.

The present inventors have discovered a process to prepare silicone vesicles having improved stability and the ability to protect loaded actives over an extended period of time.

SUMMARY OF THE INVENTION

The present invention provides a process for preparing a vesicle composition comprising;

I) first combining
   A) a non water dispersible organopolysiloxane having at least one hydrophilic substituent group,
   B) a water miscible solvent,
   then adding water to form an aqueous dispersion,
II) mixing the aqueous dispersion to form vesicles,
III) optionally, removing the water miscible solvent from the vesicles.

The present invention also relates to the vesicle compositions obtained from the inventive process, and the vesicle compositions further comprising a personal, household, health care ingredient.

The present invention further relates to personal, household, health care product compositions containing the vesicle compositions.

DETAILED DESCRIPTION OF THE INVENTION

The first step in the process of the present invention involves combining;
   A) an organopolysiloxane having at least one hydrophilic substituent group,
   B) a water miscible solvent,
   with water to form an aqueous dispersion.

Component A) is an organopolysiloxane having at least one hydrophilic substituent group. Organopolysiloxanes are well known in the art and are often designated as comprising any number of "M" siloxy units ($R_3SiO_{0.5}$), "D" siloxy units ($R_2SiO$), "T" siloxy units ($RSiO_{1.5}$), or "Q" siloxy units ($SiO_2$) where R is independently any hydrocarbon group. In the present invention, the organopolysiloxane has at least hydrophilic substituent. That is, at least one of the R hydrocarbon groups present in the organopolysiloxane is a hydrophilic group. For purposes of this invention, "hydrophilic group" is the accepted meaning in the art, i.e, designating water loving chemical moieties. Thus, the hydrophilic group can be selected from various cationic, anionic, zwitterionic, polyoxyalkylene, oxoazoline chemical moieties that are commonly used in combination with various hydrophobic chemical moieties to create surfactant structures or molecules having surface-active behavior.

The amount of the hydrophilic substituent on the organopolysiloxane can vary, depending on the specific chemical component, providing there is at least one hydrophilic group present on the organopolysiloxane. However, the amount of the hydrophilic groups present in the organopolysiloxane is such that it does not impart water solubility or water dispersibility to the organopolysiloxane. That is, when the organopolysiloxane is mixed with water at any proportions from 10/90 to 90/10 parts by weight with water, a solution, an emulsion, or stable dispersion is not formed. Rather, the organopolysiloxane of the present invention and water separate upon standing. The amount of the hydrophilic groups present on the organopolysiloxane can be described by its weight percent, or in particular, the weight percent of the organopolysiloxane and weight percent of the total hydrophilic groups present in the molecule. Typically, the weight percent of the siloxane units in the organopolysiloxane can vary from 50 to 90, alternatively from 55 to 85, or alternatively from 55 to 80 weight percent, while the remaining weight portion of the organopolysiloxane is the hydrophilic group.

In one embodiment of the present invention, the organopolysiloxane having at least one hydrophilic substituent group is selected from silicone polyethers. Silicone polyethers (SPEs) generally refer to silicones containing polyether or polyoxyalkylene groups, which encompasses many different structural forms. Two common forms are the rake-type or ABA type. In this embodiment, component (A) is a silicone polyether and can have a structure represented by:

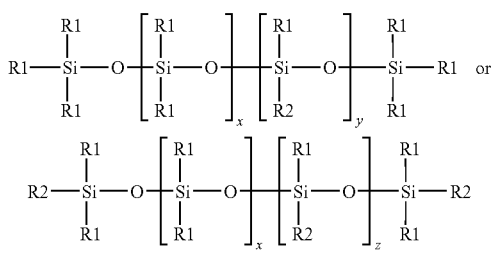

A cyclic polyether of the type shown below can also be used.

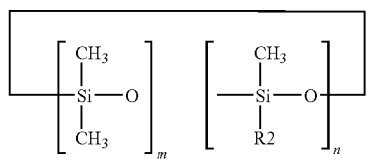

In these structures, R1 represents an alkyl group containing 1-6 carbon atoms such as methyl, ethyl, propyl, butyl, pentyl, and hexyl; R2 represents the group $-(CH_2)_aO(C_2H_4O)_b(C_3H_6O)_cR3$; x has a value of 1-1,000, alternatively 1-500, or alternatively 10-250; y has a value of 1-500, alternatively 1-100, or alternatively 2-50; z has a value of 1-500, or alternatively 1-100; m has a value of 3-5; n is one; a has a value of 3-6; b has a value of 4-20; c has a value of 0-5; and R3 is hydrogen, a methyl group, or an acyl group such as acetyl. Typically, R1 is methyl; b is 6-12; c is zero; and R3 is hydrogen.

The silicone surfactants can be prepared by any of the techniques known in the art, and many are commercially available. For example, rake type SPEs are derived most commonly from hydrosilylating SiH sites of $MD_xD'_yM$ with allyloxy-functional poly ethers in the presence of Pt catalyst.

The process of the present invention is particularly useful to prepare silicone vesicle compositions containing a silicone polyether having silicone/polyether molar ratios such that the silicone polyether aqueous solubility varies from those having only slightly water solubility or dispersibility to insoluble ones. This silicone/polyether ratio can be represented as value of x/y or x/z in the silicone polyether structures shown above and is greater than 14/1. Such silicone polyethers are prepared from a SiH functional organopolysiloxane having a D/D' greater than 14/1, where D' represents a SiH disiloxy unit (for example MeHSiO).

Component B) is a water-miscible solvent. As used herein "water-miscible" means the solvent forms a dispersion with water at room temperature for at least several hours. Furthermore, water-miscible solvent can be a volatile solvent. "Volatile" means the solvent has a higher vapor pressure than water at various temperatures. As such, when the aqueous dispersion of the organopolysiloxane and solvent are subjected to conditions to remove the solvent, such as subjecting the dispersion under reduced pressures, the solvent is primarily removed first, allowing all or most of the water to remain in the composition.

Suitable water-miscible solvents for vesicle dispersion preparation include organic solvents such as alcohols, ethers, glycols, esters, acids, diols, and the mixture of these solvents. The organic solvents should be miscible with water at the proportion and lower in order to effectively disperse silicones and maintain stable and uniform dispersion overtime. For the purpose of illustration, water-miscible alcohols include method, ethanol, propanol, isopropanol, butanol, and higher hydrocarbon alcohols; ethers include glycol ethers, methylethyl ether, methyl isobutyl ether (MIBK), etc; glycols include propylene glycols, dipropylene glycols, esters include esters of triglycerol, the esterification products of acid and alcohol. When silicone vesicles of low organic solvents are desired, typically water-miscible organic solvents are solvents with relatively low boiling points (<100° C.) or high evaporation rate, so they may be removed under vacuum with ease. The most preferred water-miscible organic solvents for this invention are volatile alcohols including methanol, ethanol, isopropanol, and propanol. These alcohols can be removed from aqueous mixtures containing silicone vesicle dispersions via vacuum stripping at ambient temperature. In applications where water-miscible solvents are acceptable, organic solvents of higher boiling points (>100° C.) or low evaporation rate are used and are remained in vesicle dispersions, so long as they do not compromise the stability of vesicles and the protection of loaded actives. In some applications, mixtures of water-miscible organic solvents of low boiling point and water-miscible organic solvents of high boiling point are used in preparation of silicone vesicles in the invention.

Components A) and B) are first mixed and then water added to the mixture. There are no special requirements or conditions needed for effecting the mixing of components A), B), and C). The mixing can be conducted in a batch, semi-continuous, or continuous process.

The amount of components A), B), and C) can vary in the process, but typically range as follows;

A) 2 to 50 wt %, alternatively 2 to 35 wt %, or alternatively 2 to 30 wt %,

B) 2 to 50 wt %, alternatively 2 to 35 wt %, or alternatively 2 to 30 wt %,

C) sufficient amount to provide the sum of the wt % of A), B), and C) to equal 100%

The amount of B) water-miscible solvent used to disperse the organopolysiloxane depends on the type of organopolysiloxane and how much hydrophilic groups are present. Typically, the aqueous mixture to effectively disperse silicones comprises of 5 to 80 parts of water miscible solvent and 5 to 95 parts of water; alternatively 5 to 60 parts of water, or alternatively 10 to 50 parts water.

Step II in the process of the present invention is mixing the aqueous dispersion formed in Step I to form vesicles. There are no special requirements or conditions needed to effect the mixing and formation of vesicles. Mixing techniques can be simple stirring, homogenizing, sonalating, and other mixing techniques known in the art to effect the formation of vesicles in aqueous dispersions. The mixing can be conducted in a batch, semi-continuous, or continuous process.

The formation of vesicles can be confirmed by techniques common in the state of the art. Typically, vesicles have a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes. For example, average particle sizes of less than 0.500 μm (micrometers), are typical for dispersed vesicles. Vesicles having an average particle size of less than 0.200 μm, or 0.100 μm are possible with the teachings of the present invention.

Step III in the process of the present invention is optional, and involves removing the water miscible volatile solvent, from a part or all of component B). Typically, the water miscible volatile solvent is removed by known techniques in the art, such as subjecting the vesicle composition to reduced pressures, while optionally heating the composition to slightly elevated temperatures, for example up to 50° C. Devices illustrative of such techniques include rotary evaporators and thin film strippers.

The present invention also relates to the vesicle compositions produced by the methods, as described supra. The formation of vesicles can be confirmed by techniques common in the state of the art. Typically, vesicles having a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes. For example, average particle sizes of less than 0.500 μm (micrometers), are typical for dispersed vesicles. Vesicles having a average particle size of less than 0.200 μm, or 0.100 μm are possible with the method of the present invention.

The present invention further relates to vesicle compositions further comprising a personal, household, or health care ingredient. Thus, the vesicle compositions can be used to entrap, and subsequently deliver after application, a personal, household care, or health care ingredient. A listing of possible personal, household, or health care ingredients is taught in WO 03/101412, which is incorporated herein by reference. The personal or health care ingredient can also be selected from a personal or health care "active", that is, any compound known to have either cosmetic and/or pharmaceutical activity. A representative listing of such personal or health care actives are disclosed in U.S. Pat. No. 6,168,782, which is hereby incorporated by reference.

Compositions prepared according to the invention can be used in various over-the-counter (OTC) personal care compositions, health care compositions, and household care compositions, but especially in the personal care arena. Thus, they can be used in antiperspirants, deodorants, skin creams, skin care toners, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, hair cuticle coats, make-ups, color cosmetics, foundations, blushes, lipsticks, lip balms, eyeliners, mascaras, oil removers, skin care cleansers, color cosmetic removers, nail polishes, and powders.

EXAMPLES

The following examples are presented to further illustrate the compositions and methods of this invention, but are not to be construed as limiting the invention. All parts and percentages in the examples are on a weight basis and all measurements were obtained at about 23° C., unless indicated to the contrary.

The vesicle compositions were analyzed via Cyro-TEM techniques according to the following procedure. Around 2.3 μl of aqueous sample solution was loaded using a micropipette on a lacey carbon film coated Cu TEM grid that was cleaned and rinsed with acetone and chloroform. The samples were diluted to about 5% solution with de-ionized water. The excess fluid on the grid surface was removed by blotting the surface with a filter paper for 1.5 second to make an aqueous thin film for TEM. The grid was then plunged into a liquid ethane contained in a small vessel located in a larger liquid nitrogen vessel under −175° C. atmosphere in the cryo-plunge system to vitrify the water film on the grid and to avoid water crystallization. The quenched sample grid was transferred in to the cryo-grid box in the cryo-plunge system. The grid box containing the sample was transferred into a Gatan cryo-transfer system filled with liquid nitrogen and loaded in a cryo-TEM stage, which has been positioned in the cryo-transfer system and cooled down to below −160° C. The sample was loaded in TEM (JEOL 2000FX) and the images were observed at below −160° C. A much colder finger, cooled to −180° C. in TEM using liquid nitrogen, was present to reduce any possible contamination on the cold specimen surface under high vaccum during TEM analysis. The digital images, as shown herein, were taken using a Gatan CCD camera attached at the bottom of the TEM column and Digital Micrograph software.

Example 1

Reference Example

Silicone Polyethers Used for Preparation of Vesicle Dispersions

A series of silicone polyethers were prepared, as illustrated in Table 1 below. This series were "rake type" silicone polyethers since they were derived from various dimethyl-methylhydrogen-polysiloxanes of the general formula, $MD_xD'_yM$ and allyloxy polyethers. The $MD_xD'_yM$ siloxanes were prepared according to known techniques. The silicone polyethers were prepared using well known platinum catalyzed hydrosilylation techniques, such as those disclosed in U.S. Pat. No. 2,823,218.

The D/D' ratio corresponds to x/y ratio in the formula $MD_xD'_yM$ and total DP is the sum of x and y. EO7 is allyoxyl poly(ethylene oxide) having about seven EO repeat units, and EO12 is allyoxyl poly(ethylene oxide) having about 12 EO repeat units; both were obtained from Dow Chemical Company (Midland, Mich.).

TABLE 1

| Siloxane structure | $MD_{27}D'_3M$ | $MD_{22}D'_2M$ | $MD_{28.12}D'_{1.88}M$ | $MD_{46.88}D'_{3.12}M$ | $MD_{70}D'_3M$ |
|---|---|---|---|---|---|
| D/D' ratio | 9.0 | 11 | 15 | 15 | 23.3 |
| Total dp, D + D' | 30 | 24 | 30 | 50 | 73 |
| EO7 polyether | | SPE 1 | SPE 2 | SPE 3 | |
| EO12 polyether | SPE 4 | SPE 5 | SPE 6 | SPE 7 | SPE 8 |

For $MD_xD'_yM$ rake-type SPEs, D/D' ratio represents the relative ratio of the number of siloxane repeat units to the number of polyether substituted units on the siloxane polyethers, and a direct measure of hydrophobic to hydrophilic ratio of the SPEs. The lower the D/D' ratio, the more hydrophilic the SPEs, and more readily dispersible the SPE is in water.

Example 2

Effect of D/D' Ratio of SPEs and Alcohol on Vesicle Dispersion Preparation

SPEs were generally found to spontaneously disperse in water, forming vesicles, when the D/D' was 12 or lower, as summarized in Table 2 below. When the D/D' ratio of the SPE was 15 or higher, the SPEs were less dispersible in water, and the rate of SPE dispersion in water could be very slow to incomplete. This example demonstrates the time needed to disperse SPE 6 (from Example 1) in water and how much faster it disperses when a small amount of isopropanol was present.

When D/D' was greater than 15, the SPEs did not spontaneously disperse in water. For example, the SPEs derived from $MD_{70}D'_3M$ (such as SPE 8) were not dispersible at all in water, even over more than a period of 2 months.

Examples 2A and 2B show how SPE 6, a silicone polyether of $MD_{28.12}D'_{1.88}M$ siloxane structure dispersed in water alone and in the presence of 5% isopropanol, respectively. It took about 3 weeks of continuous mixing to form a homogeneous dispersion in water as opposed to less than 1 day when 5% by weight of isopropanol present in water.

Homogeneous dispersions of SPE 3 and SPE 7, silicone polyethers of $MD_{46.88}D'_{3.12}M$ siloxane backbone with D/D' of 15, were also made into homogeneous dispersions within 2 days with aid of 5% isopropanol, as shown in Examples 2C and 2D.

TABLE 2

| Example | 2A | 2B | 2C | 2D |
|---|---|---|---|---|
| Process History | 3 weeks of continuous mix | As mixed, uniform dispersion in 1 day | As mixed, homogeneous in 2 days | As mixed, uniform dispersion in 2 days |
| Formulation | | | | |
| SPE 3 (D/D' = 15), g | | | 10 | |
| SPE 6 (D/D' = 15), g | 10.02 | 10.09 | | |
| SPE 7, (D/D' = 15) g | | | | 10.03 |
| Isopropanol, g | | 5.02 | 5.000 | 5.02 |
| D.I. Water, g | 90.030 | 85.3 | 85.000 | 85.3 |
| Final Dispersion Composition | | | | |
| Wt. % SPE | 10.00 | 10.00 | 10.00 | 10.00 |
| Wt. % Isopropanol | 0.00 | 5.00 | 5.00 | 5.00 |
| Wt. % Water | 90.00 | 85.00 | 85.00 | 85.00 |
| pH of the dispersion | 5.99 | 6.52 | 6.2 | 6.22 |
| Avg. dispersion size, um | | | | |
| D(v, 0.5), μm | | | | |
| D(v, 0.9), μm | | | | |

Cryo-TEM images confirmed vesicles were formed in Examples 2A, 2B, and 2D. The images showed the presence of single lamellar vesicles in Example 2A, and presence of multi-lamellar vesicles in Examples 2B and 2D.

Example 3

Comparative Example

A dispersion of SPE 8 in water was attempted by incorporating 10.0 g of SPE 8 into 90.0 g of de-ionized water in a glass jar. The jar was subjected to mixing on a rotowheel mixer. Even after 4 weeks of mixing the SPE remained as separated in water, no dispersion was formed.

Example 4

Preparation of 20% and 30% SPE 8 Vesicle Dispersions

Example A4

Vesicle Dispersion of 14.4% SPE 8 Dispersion in 28.7% Isopropanol and 56.9% Water A dispersion was prepared by first adding SPE 8 into isopropanol with continuous mixing. Then, water was gradually added with continuous stirring. The resulting final mixture was clear, and a homogenous dispersion. SPE vesicles of 31 nm average sizes were observed and the dispersion has a clear water-like appearance due to the size of the vesicles.

Example 4B

Vesicle Dispersion of 20.0% SPE 8 in 80.0% Water

A homogeneous dispersion of SPE 8 in isopropanol and water was prepared, following a similar procedure for Example 4A. This dispersion was further stripped under vacuum at ambient temperature to remove volatile isopropanol using a Rotovapor. The theoretical amount of 74.93 g of IPA was completely removed and yielded a theoretically alcohol-free aqueous dispersion of SPE 8 vesicles. The resultant product was a milky-white, homogeneous dispersion with an average particle size of 212 nm, as measured by Nanotrac particle analyzer.

Example 4C

Vesicle Dispersion of 21.2% SPE 8 in 28.8% Isopropanol and 50% Water

A homogeneous vesicular dispersion of 21 nm average particle size in isopropanol and water was prepared, following a procedure similar to that of Example 4A.

Example 4D

Vesicle Dispersion of 29.5% SPE 8 in 1.0% Isopropanol and 69.5% Water

A homogeneous vesicular dispersion of 436 nm average particle size in water was prepared, following a procedure similar to that of Example 4B. The final mixture was a milky-white, homogenous dispersion.

Example 5

Effect of Isopropanol Concentration on Vesicle Dispersion Size

The ease of dispersing silicone polyethers and, in some cases, the size and structure of the vesicles in the final water dispersions depends on the amount of isopropanol. This example illustrates this effect with two rake-type SPEs, SPE 7 and 8 as identified in Example 1.

Examples 5A, 5B, and 5C

Dispersions of SPE 8 in water containing 5% to 20 wt. % isopropanol were prepared according to the procedure described previously, according to the formulations summarized in Table 5. Example 5C was prepared by subjecting the Example 5B dispersion to further vaccum stripping to remove most of the IPA.

Examples 5D and 5E

A homogeneous vesicle dispersion of SPE 7 was made in 20% IPA and 70% water having an average dispersion size of only 77 nm, according to the previously described procedure, as summarized as Example 5D. The isopropanol was the removed by vacuum stripping, resulting in a dispersion (Example 5E) having an average dispersion size of only 49 nm in water, as summarized in Table 5.

| Example # | 4A | 4B | 4C | 4D |
|---|---|---|---|---|
| Process History | As mixed | Mixed, then stripped | As mixed | Mixed, then stripped |
| SPE 8, g | 43.11 | 37.59 | 64.12 | 55.89 |
| IPA, g | 86.23 | 74.93 | 87.00 | 75.93 |
| D.I. Water, g | 170.724 | 148.55 | 151.268 | 131.82 |
| Batch size, as mixed | 300 | 261.07 | 302.4 | 263.64 |
| IPA removed, G | | −75.70 | | −74.10 |
| Final batch, after strip | | 185.37 | | 189.53 |
| Wt. % Polymer | 14.4 | 20.0 | 21.2 | 29.5 |
| Wt. % IPA | 28.7 | 0.0 | 28.8 | 1.0 |
| Wt. % Water | 56.9 | 80.0 | 50.0 | 69.5 |
| Appearance of dispersion | Clear water-like liquid | Milky white material | Clear water-like liquid | Milky white material |
| Avg. particle size, μm | 0.031 | 0.212 | 0.021 | 0.436 |
| D(v, 0.5), μm | 0.029 | 0.178 | 0.019 | 0.353 |
| D(v, 0.9), μm | 0.044 | 0.428 | 0.036 | 0.914 |

TABLE 5

| Example # | 5A | 5B | 5C | 5D | 5E |
|---|---|---|---|---|---|
| Process History | As mixed | As mixed | Mixed, then stripped | As mixed | Mixed, then stripped |
| SPE 8, g | 10.025 | 30.012 | 20 | | |
| SPE 7, g | | | | 30.006 | 20.0 |
| IPA, g | 10.005 | 60.082 | 10 | 60.172 | 40.0 |
| D.I. Water, g | 80.044 | 210.063 | 140 | 210.757 | 140.0 |
| Final Dispersion Composition | | | | | (~40 g alcohol) |
| Wt. % Polymer | 10.02 | 10.00 | 11.76 | 9.97 | 12.50 |
| Wt. % IPA | 10.00 | 20.02 | 5.88 | 20.00 | 0.00 |
| Wt. % Water | 79.98 | 69.98 | 82.35 | 70.03 | 87.50 |
| pH of the dispersion | 5.87 | 7.14 | 6.81 | 6.35 | 6.38 |
| Avg. dispersion size, μm | 1.427 | 0.106 | 0.099 | 0.077 | 0.049 |
| D(v, 0.5), μm | 0.955 | 0.092 | 0.091 | 0.071 | 0.072 |
| D(v, 0.9), μm | 3.789 | 0.178 | 0.156 | 0.112 | 0.104 |

Cryo-TEM images confirmed the silicone polyether dispersions were nano-scale vesicles and aggregates of vesicles. The actual sizes observed were consistent with the particle size measured by Nanotrac particle analyzer.

Example 6

SPE Vesicle Dispersions Containing Vitamin A Palmitate

The method of this invention can also be used to entrap and retain oil-soluble substances into vesicles in aqueous dispersions. This is very desirable and beneficial utility of vesicles and vesicular aggregates prepared from silicone polyethers. As many personal care actives & ingredients are not water-soluble or not water-compatible. This makes it not practical to incorporate such ingredients as vitamins, fragrances, sunscreens, and oils directly into water-based or water-continuous end-product formulations, such as creams, lotions, gels, etc.

This series of examples shows that vitamin A palmitate (a preferred form of vitamin A for skin care products) can be successfully incorporated into SPE based vesicles in water dispersions, using the method of this invention. Results and formulations are summarized in Table 6.

Examples 6A and 6B

Vitamin A Plamitate Entrapped SPE Vesicles in Partially and Fully Stripped Aqueous Dispersions Vitamin A palmitate (VAP) was first dispersed in isopropanol at 50/50 ratio by weight to keep VAP in a liquid form for ease of mixing. The VAP/IPA was then mixed in with SPE 8, followed by incorporation of isopropanol to form a homogeneous mixture. While under continuous mixing, water was gradually and continuously incorporated into the mixture containing the SPE, VAP and IPA. Then, the mixture was homogenized, using an APV benchtop homogenizer, to further narrow and reduce the dispersion size. The homogenized dispersion was subsequently stripped to remove isopropanol under vaccum at ambient temperature, using a Rotovapor.

The 6A example was a partially stripped dispersion having about 10% IPA remaining and an average dispersion size of 0.229 um. The 6B example was a fully stripped dispersion containing 20.8% SPE, 4.5% VAP, 2.2% IPA and 72.5% water. Example 6B was a homogeneous, beige milky dispersion having an average vesicle size of 0.974 um.

Example 6C

Vitamin A Palmitate Loaded Dispersion Made without Homogenization Using Ethano This dispersion was prepared by first dispersing vitamin A palmitate into SPE 8 in the presence of a small quantity of ethanol. The prescribed amount of ethanol was mixed in with SPE/VAP to form a homogeneous mixture. While under continuous mixing, water was gradually and continuously incorporated into the mixture. A homogeneous mixture was obtained. The mixture was then subjected to vaccum stripping to remove the volatile alcohol. The final dispersion had a composition of 4.5% VAP, 20.7% SPE, 2.9% EtOH and 72.0% water. The dispersion had an average dispersion size of 0.763 um.

Examples 6D and 6E

Vitamin A Palmitate Loaded Dispersions Made with EtOH

Ethanol was used as dispersing aid to prepare these VAP loaded SPE vesicles in water dispersions. The procedures followed the ones that used to make Example 6A and 6B, except EtOH used in place of IPA. The final dispersion compositions are shown in Table 6. The two dispersions had an average dispersion size of 0.284 um and 0.331 um, respectively.

TABLE 6

| Example # | 6A | 6B | 6C | 6D | 6E |
|---|---|---|---|---|---|
| Alcohol type used | IPA | IPA | EtOH | EtOH | EtOH |
| Process History | Mixed, Homog., Partially Stripped | Mixed, Homog., Fully Stripped | Mixed, Stripped | Mixed, Homog., Partially Stripped | Mixed, Homog., Fully Stripped |
| VAP (vitamin A palmitate), g | 3.96 | 3.91 | 9.89 | 3.94 | 3.69 |
| Alcohol, g | 32.71 | 32.32 | 81.61 | 32.54 | 30.50 |
| SPE 8, g | 18.35 | 18.13 | 45.73 | 18.23 | 17.09 |

TABLE 6-continued

| Example # | 6A | 6B | 6C | 6D | 6E |
|---|---|---|---|---|---|
| Water, g | 63.96 | 63.19 | 159.01 | 63.40 | 59.42 |
| Batch size, as mixed, g | 118.97 | 117.55 | 296.23 | 118.11 | 110.70 |
| Alcohol Removed, g | 23.48 | 30.37 | 75.30 | 22.21 | 28.47 |
| Batch size, after strip, g | 95.49 | 87.18 | 220.93 | 95.90 | 82.23 |
| Final Dispersion composition | | | | | |
| Wt, % VAP | 4.1 | 4.5 | 4.5 | 4.1 | 4.5 |
| Wt. % Alcohol | 9.7 | 2.2 | 2.9 | 10.8 | 2.5 |
| Wt. % SPE Polymer | 19.2 | 20.8 | 20.7 | 19.0 | 20.8 |
| Wt. % Water | 67.0 | 72.5 | 72.0 | 66.1 | 72.3 |
| Appearance of Dispersion | Beige milky dispersion | Beige milky dispersion | Beige milky dispersion; small oil droplets atop | Beige milky dispersion | Beige milky dispersion |
| Average particle size, μm | 0.2291 | 0.974 | 0.763 | 0.2842 | 0.331 |
| D(v, 0.5), μm | 0.1602 | 0.995 | 0.374 | 0.1624 | 0.2103 |
| D(v, 0.9), μm | 0.513 | 1.783 | 1.987 | 0.727 | 0.785 |

The invention claimed is:

1. A process for preparing a vesicle composition consisting of;
   I) first combining
      A) a non water dispersible organopolysiloxane having at least one hydrophilic substituent group,
      B) a water miscible solvent,
      then adding water to form an aqueous dispersion,
   II) mixing the aqueous dispersion to form vesicles,
   III) optionally, removing the water miscible solvent from the vesicles.

2. The process of claim 1 wherein the aqueous dispersion consists of;
   A) 2 to 50 wt % of the organopolysiloxane,
   B) 2 to 50 wt % of the water miscible solvent,
   C) sufficient amount of water
      to provide the sum of the wt % of A), B), and C) to equal 100 wt %.

3. The process of claim 1 wherein the organopolysiloxane is a silicone polyether.

4. The process of claim 1 wherein the organopolysiloxane is a silicone polyether having a structure represented by:

$$R_1-\underset{\underset{R_1}{|}}{\overset{\overset{R_1}{|}}{Si}}-O\left[\underset{\underset{R_1}{|}}{\overset{\overset{R_1}{|}}{Si}}-O\right]_x\left[\underset{\underset{R_2}{|}}{\overset{\overset{R_1}{|}}{Si}}-O\right]_y\underset{\underset{R_1}{|}}{\overset{\overset{R_1}{|}}{Si}}-R_1 \text{ or}$$

$$R_2-\underset{\underset{R_1}{|}}{\overset{\overset{R_1}{|}}{Si}}-O\left[\underset{\underset{R_1}{|}}{\overset{\overset{R_1}{|}}{Si}}-O\right]_x\left[\underset{\underset{R_2}{|}}{\overset{\overset{R_1}{|}}{Si}}-O\right]_z\underset{\underset{R_1}{|}}{\overset{\overset{R_1}{|}}{Si}}-R_2$$

where R1 represents an alkyl group containing 1-6 carbon atoms;
R2 represents the group $-(CH_2)_aO(C_2H_4O)_b(C_3H_6O)_cR_3$;
x is 1-1,000; y is 1-500; z is 1-500; a is 3-6; b is 4-20; c is 0-5;
and R3 is hydrogen, a methyl group, or an acyl group.

5. The process of claim 1 wherein the silicone polyether has the structure, $$R_1-\underset{\underset{R_1}{|}}{\overset{\overset{R_1}{|}}{Si}}-O\left[\underset{\underset{R_1}{|}}{\overset{\overset{R_1}{|}}{Si}}-O\right]_x\left[\underset{\underset{R_2}{|}}{\overset{\overset{R_1}{|}}{Si}}-O\right]_y\underset{\underset{R_1}{|}}{\overset{\overset{R_1}{|}}{Si}}-R_1$$

x is from 1 to 1000, y is from 1 to 500, R1 is methyl,
R2 represents the group $-(CH_2)_aO(C_2H_4O)_b(C_3H_6O)_cR_3$ where a is 3-6; b is 4-20; c is 0-5, and R3 is hydrogen, a methyl group, or an acyl group.

6. The process of claim 5 wherein the ratio of x/y is greater than 14/1.

7. The process of claim 1 wherein the water miscible solvent is a volatile solvent.

8. The process of claim 1 wherein the water miscible solvent is an alcohol.

9. The process of claim 1 wherein the water miscible volatile solvent is isopropyl alcohol or ethyl alcohol.

10. The product resulting from the process of any one of claims 1-9.

* * * * *